(12) United States Patent
Wilkinson et al.

(10) Patent No.: US 7,644,629 B2
(45) Date of Patent: Jan. 12, 2010

(54) TENSILE SPECIMEN MEASURING APPARATUS AND METHOD

(75) Inventors: Carey E. Wilkinson, O'Fallon, MO (US); William Lamey, III, St. Peters, MO (US)

(73) Assignee: The Boeing Company, Chicago, IL (US)

( * ) Notice: Subject to any disclaimer, the term of this patent is extended or adjusted under 35 U.S.C. 154(b) by 70 days.

(21) Appl. No.: 12/029,714

(22) Filed: Feb. 12, 2008

(65) Prior Publication Data

US 2009/0199652 A1 Aug. 13, 2009

(51) Int. Cl.
*G01N 3/08* (2006.01)
(52) U.S. Cl. .......................................... 73/826; 73/760
(58) Field of Classification Search ............ 73/760–862
See application file for complete search history.

(56) References Cited

U.S. PATENT DOCUMENTS 4,490,202 A * 12/1984 Dumont ....................... 156/166
6,523,419 B1 * 2/2003 Nonaka et al. ................. 73/827

* cited by examiner

*Primary Examiner*—Max Noori
(74) *Attorney, Agent, or Firm*—Tung & Associates

(57) ABSTRACT

A tensile specimen measuring apparatus includes a generally elongated base, a generally elongated pin channel provided in the base, a measuring pin carrier slidably mounted in the pin channel of the base, at least one contact pin carried by the measuring pin carrier, at least one contact pin disposed at an end of the pin channel of the base in generally spaced-apart relationship with respect to the at least one contact pin carried by the measuring pin carrier and an electronic measuring device engaging the at least one contact pin carried by the measuring pin carrier. A tensile specimen measuring method is also disclosed.

20 Claims, 5 Drawing Sheets

TENSILE SPECIMEN MEASURING APPARATUS AND METHOD

TECHNICAL FIELD

The disclosure relates to tensile measurements of specimens. More particularly, the disclosure relates to a tensile specimen measuring apparatus and method which facilitate electronic data entry of tensile specimen geometry measurements prior to tensile testing.

BACKGROUND

Prior to tensile testing of specimens, the geometrical dimensions of the specimens, such as the width and thickness, for example and without limitation, may be measured. Conventional geometrical measurement of specimens may include measuring the specimen manually using a micrometer and entering the data by hand. However, the conventional geometrical measurement techniques may be time-consuming, labor-intensive and not ergonomically-friendly. Furthermore, the measuring anvil on a micrometer may be excessively wide to measure the centerline of the tensile specimen.

SUMMARY

The disclosure is generally directed to a tensile specimen measuring apparatus. An illustrative embodiment of the apparatus includes a generally elongated base, a generally elongated pin channel provided in the base, a measuring pin carrier slidably mounted in the pin channel of the base, at least one contact pin carried by the measuring pin carrier, at least one contact pin disposed at an end of the pin channel of the base in generally spaced-apart relationship with respect to the at least one contact pin carried by the measuring pin carrier and an electronic measuring device engaging the at least one contact pin carried by the measuring pin carrier.

The disclosure is further generally directed to a tensile specimen measuring method. An illustrative embodiment of the method includes providing an electronic measurement device, zeroing the electronic measurement device, providing a test specimen measuring apparatus having at least two contact pins, inserting a test specimen between the at least two contact pins of the test specimen measuring apparatus, measuring a parameter of the test specimen by drawing the test specimen between the at least two contact pins and electronically recording a measurement reading displayed on the electronic measuring device.

BRIEF DESCRIPTION OF THE ILLUSTRATIONS

DETAILED DESCRIPTION

Figure 1:
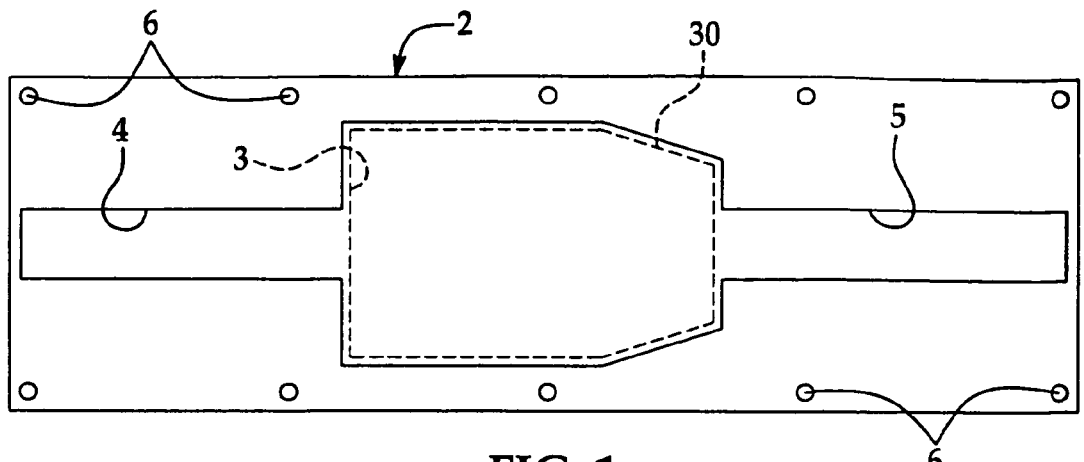
FIG. 1 is a top view of a base component of an illustrative embodiment of the tensile specimen measuring apparatus.
Figure 5:
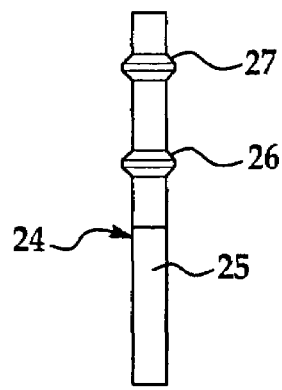
FIG. 5 is a side view of a contact pin component of an illustrative embodiment of the tensile specimen measuring apparatus.
Figure 6:
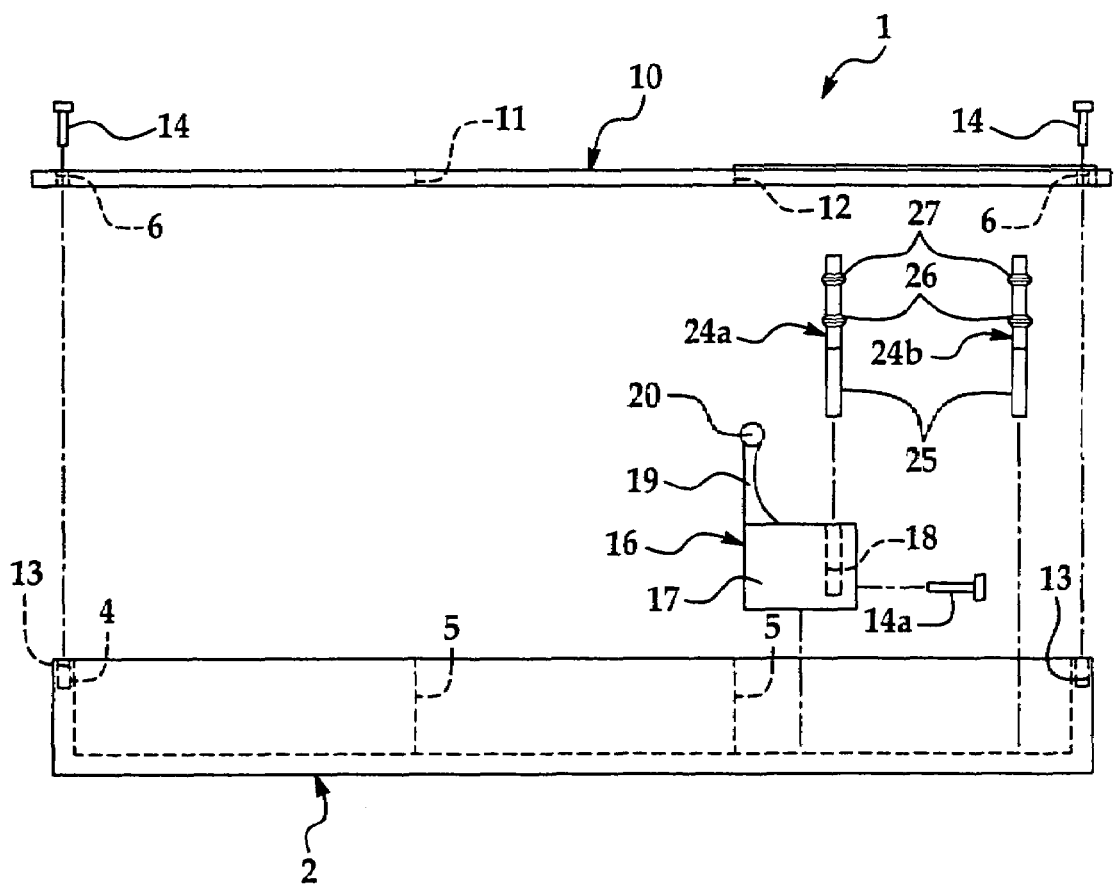
FIG. 6 is an exploded side view of an illustrative embodiment of the tensile specimen measuring apparatus.
Figure 7:
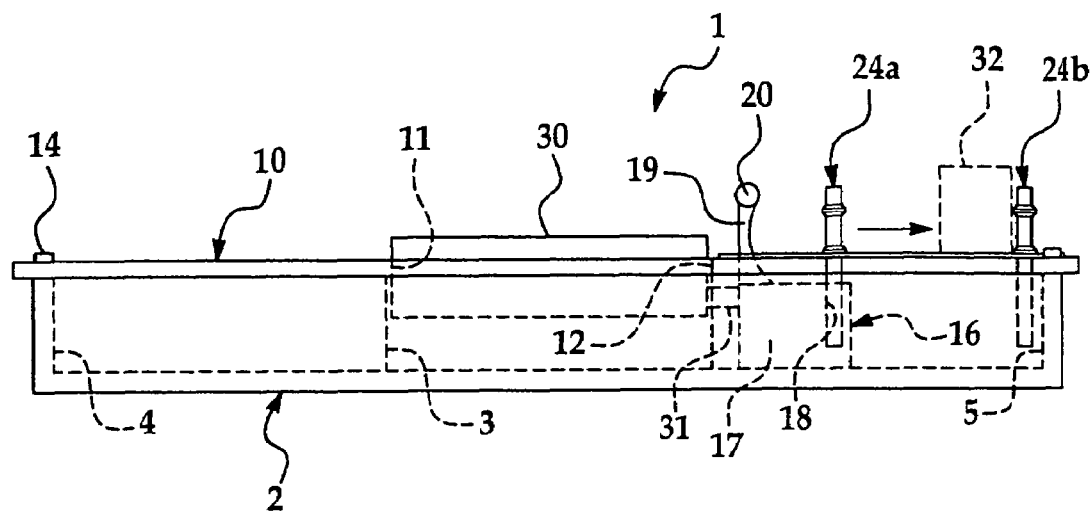
FIG. 7 is a side view of an illustrative embodiment of the assembled tensile specimen measuring apparatus, with an electronic measuring device placed on the apparatus, more particularly illustrating initial positioning of a pair of contact pins on the apparatus.
Figure 8:
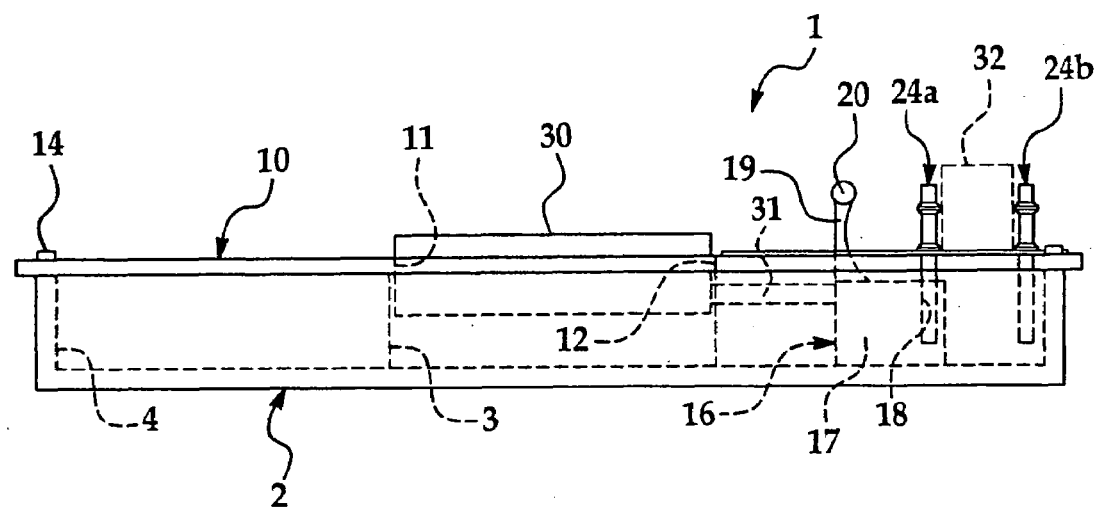
FIG. 8 is a side view of an illustrative embodiment of the assembled tensile specimen measuring apparatus, with an electronic measuring device placed on the apparatus, more particularly illustrating positioning of the contact pins against respective sides of a test specimen (shown in phantom).

Referring initially to FIGS. 1-8, an illustrative embodiment of the tensile specimen measurement apparatus, hereinafter apparatus, is generally indicated by reference numeral 1. The apparatus 1 is shown in exploded view in FIG. 6 and in assembled form in FIGS. 7 and 8. The apparatus 1 may include a base 2 which may have a generally elongated, rectangular shape. Rubber bumper feet (not shown) may be provided on the bottom four corners of the base 2. As shown in FIGS. 1, 7 and 8, a measuring device cavity 3 may be provided in the base 2. A rear slot 4 and a pin channel 5 may extend from rear and front ends, respectively, of the measuring device cavity 3. As shown in FIG. 1, the measuring device cavity 3 may be sized and shaped to accommodate an electronic measuring device 30 (shown in phantom) which is adapted to measure the geometrical dimensions of a test specimen 32 (FIGS. 7 and 8), as will be hereinafter described, prior to determining the tensile strength of the test specimen 32. The electronic measuring device 30 may be conventional in design.

Figure 2:
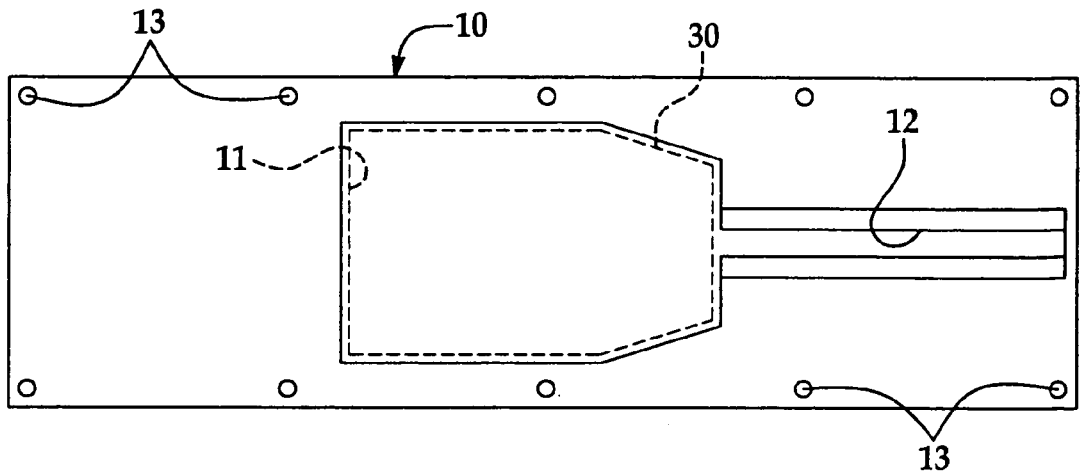
FIG. 2 is a top view of a cover plate component of an illustrative embodiment of the tensile specimen measuring apparatus.

A cover plate 10 may be provided on the base 2. As shown in FIG. 2, a measurement device opening 11 which generally registers with the measurement device cavity 3 of the base 2 may extend through the cover plate 10. An elongated pin slot 12 may extend through the cover plate 10 from the measurement device opening 11 and in generally registering relationship with respect to the pin channel 5 in the base 2. The cover plate 10 may be detachable with respect to the base 2 according to any suitable technique which is known to those skilled in the art. As further shown in FIG. 1, in some embodiments multiple base fastener openings 6 may extend into the base 2 around the perimeter thereof. As shown in FIG. 2, multiple plate fastener openings 13 may extend through the cover plate 10 in registering relationship with respect to the respective base fastener openings 6 in the base 2. Therefore, as shown in FIG. 6, plate fasteners 14 may be extended through the respective base fastener openings 6 in the cover plate 10 and into the respective registering plate fasteners 13 provided in the base 2.

Figure 3:
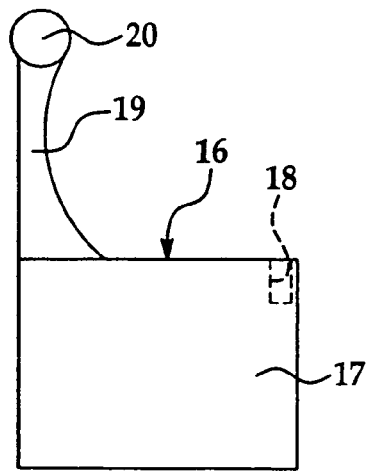
FIG. 3 is a side view of a measuring pin carrier component of an illustrative embodiment of the tensile specimen measuring apparatus.
Figure 4:
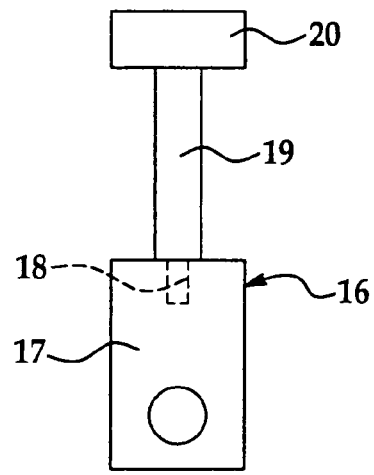
FIG. 4 is a front view of a measuring pin carrier component of an illustrative embodiment of the tensile specimen measuring apparatus.

A measuring pin carrier 16 includes a pin carrier body 17 which is slidably mounted in the measuring device cavity 3 of the base 2. As shown in FIGS. 3 and 4, a pin opening 18 may be provided in the pin carrier body 17 of the measuring pin carrier 16. A generally elongated handle support 19, on which is provided a handle 20, may extend from the pin carrier body 17. When the cover plate 10 is placed on the base 2, as shown in FIGS. 7 and 8, the handle support 19 may extend through the pin channel 5 of the base 2 and through the registering pin slot 12 of the cover plate 10.

}

As further shown in FIGS. 7 and 8, a first contact pin 24a may be seated in the pin opening 18 provided in the pin carrier body 17 of the measuring pin carrier 16. The first contact pin 24a may extend from the pin channel 5 of the base 2 and through the registering pin slot 12 of the cover plate 10. A second contact pin 24b may extend from the pin channel 5 of the base 2 and through the pin slot 12 of the cover plate 10 generally at or adjacent to the end of the base 2 and the cover plate 10. As shown in FIG. 5, each contact pin 24 may include an elongated contact pin shaft 25. A lower pin flange 26 and an upper pin flange 27, each of which may be double-chamfered, may be provided in spaced-apart relationship with respect to each other on the contact pin shaft 25. Therefore, as shown in FIGS. 7 and 8, the first contact pin 24a may be selectively moved toward or away from the stationary second contact pin 24b by bidirectional sliding movement of the measuring pin carrier 16 in the pin channel 5 of the base 2 and the pin slot 12 of the cover plate 10. Adjustment set screws (not shown) for the contact pins 24a, 24b may be accessed through the bottom of the pin carrier 16 and the bottom of the base 2, respectively. The exact spacing between lands (26, 27) on measuring pins (24a, 24b) is very important.

In typical application, the apparatus 1 may be used to measure the geometric dimensions of a specimen 32 (shown in phantom in FIGS. 7 and 8) prior to tensile testing of the specimen 32. Accordingly, the cover plate 10 may be detached and removed from the base 2. The measuring pin carrier 16, having the first contact pin 24a seated in the pin opening 18 thereof, may be placed in the pin channel 5 of the base 2. The second contact pin 24b may also be placed in the pin channel 5 of the base 2, typically at or adjacent to the end of the base 2. The cover plate 10 may then be replaced on the base 2 and secured thereto such as by using the plate fasteners 14, for example and without limitation, as was heretofore described.

The electronic measuring device 30, which may be conventional, may be cleared or "zeroed" and seated in the measuring device opening 11 of the cover plate 10 and the underlying measuring device cavity 3 of the base 2, as shown in FIGS. 7 and 8 and in phantom in FIGS. 1 and 2. The electronic measuring device 30 may be conventional and may include an extendable measuring probe 31, as shown in phantom in FIGS. 7 and 8. As shown in FIG. 7, the test specimen 32 (shown in phantom) may be placed on the cover plate 10, against the second contact pin 24b. The measurement pin carrier 16 and first contact pin 24a may then be slid in the pin channel 5 of the base 2 and the pin slot 12 of the cover plate 10 toward the test specimen 32, as indicated by the arrow in FIG. 7, until the first contact pin 24a contacts the test specimen 32, which is interposed between the first contact pin 24a and the second contact pin 24b, as shown in FIG. 8. This may be accomplished by grasping the handle 20 of the measurement pin carrier 16, for example and without limitation. The measuring probe 31 of the electronic measuring device 30 may be fastened to the measuring pin carrier 16, as shown in FIG. 8, such as via a fastener 14a as shown in FIG. 6. Based on the position of the measuring pin carrier 16 along the pin channel 5 of the base 2, the electronic measuring device 30 measures and electronically records the distance between the first contact pin 24a and the second contact pin 24b, and therefore, the width or thickness of the test specimen 32. The process may be repeated to measure additional geometrical dimensions of the test specimen 32, as deemed necessary.

It will be appreciated by those skilled in the art that the apparatus 1 is capable of measuring dimensions of test specimens 32 having various sample sizes (width, thickness, gage length, etc.). The contact pins 24a, 24b and cover plate 10/stand-off shims (not shown) may be exchangeable depending on the particular application of the apparatus 1. In some embodiments, a self-retractable dust shield (not shown) may track in the pin slot 12 of the dust cover 10 and/or the pin carrier channel 5 of the base 2.

Figure 9:
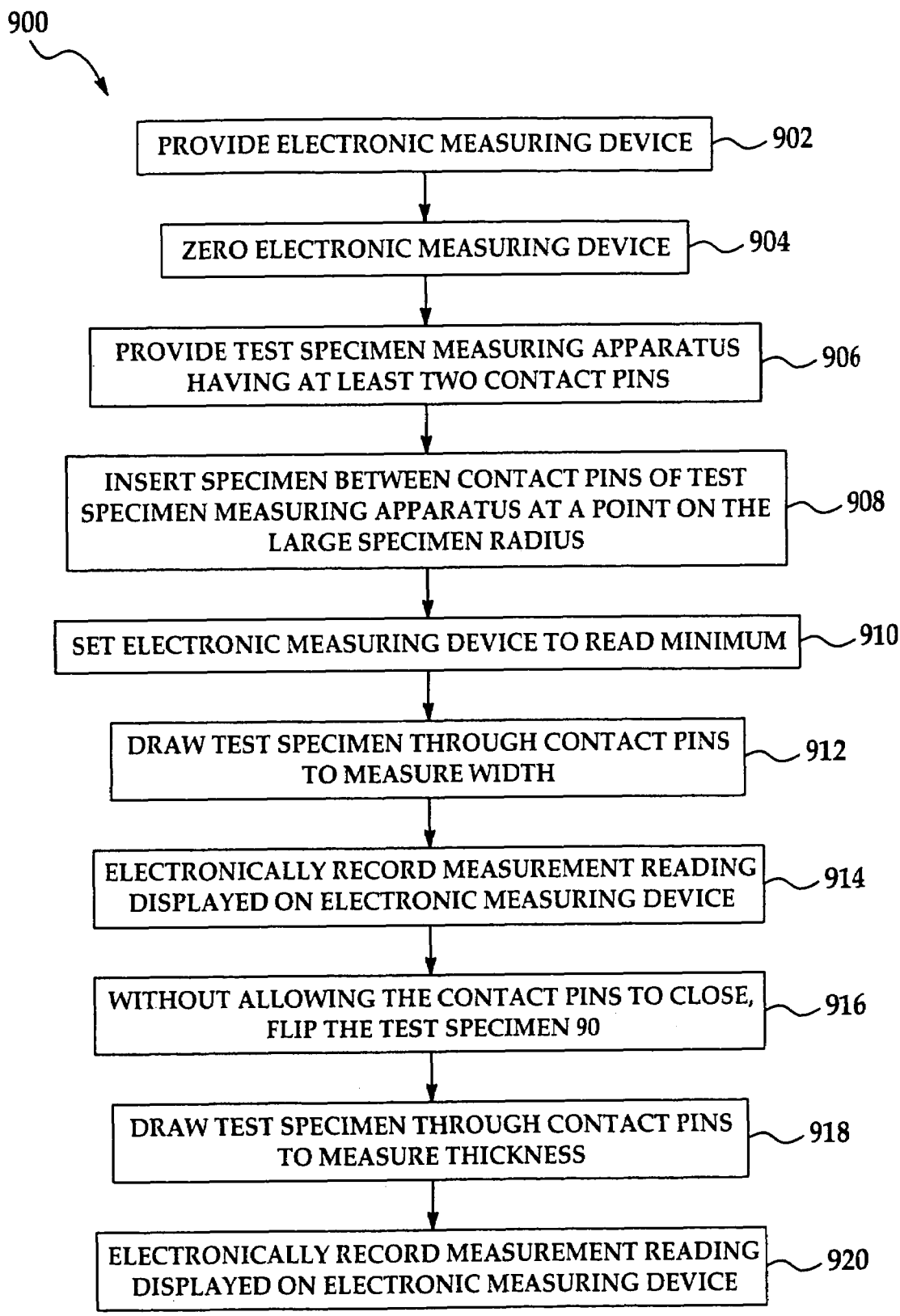
FIG. 9 is a flow diagram of an illustrative embodiment of a tensile specimen measuring method.

Referring next to FIG. 9, a flow diagram 900 of an illustrative embodiment of a tensile specimen measuring method is shown. In block 902, an electronic measuring device is provided. In block 904, the electronic measuring device may be cleared or "zeroed". In block 906, a test specimen measuring apparatus having at least two contact pins may be provided. In block 908, a test specimen may be inserted between the contact pins of the test specimen measuring apparatus at a point on the large specimen radius. In block 910, the electronic measuring device may be set to read minimum. In block 912, the test specimen may be drawn through or between the contact pins to measure width of the test specimen. In block 914, the measurement reading which is displayed on the electronic measuring device may be electronically recorded. In block 916, the test specimen may be flipped 90° without allowing closing of the contact pins. In block 918, the test specimen may be drawn through or between the contact pins to measure thickness of the test specimen. In block 920, the measurement reading displayed on the electronic measuring device may be electronically recorded.

Figure 10:
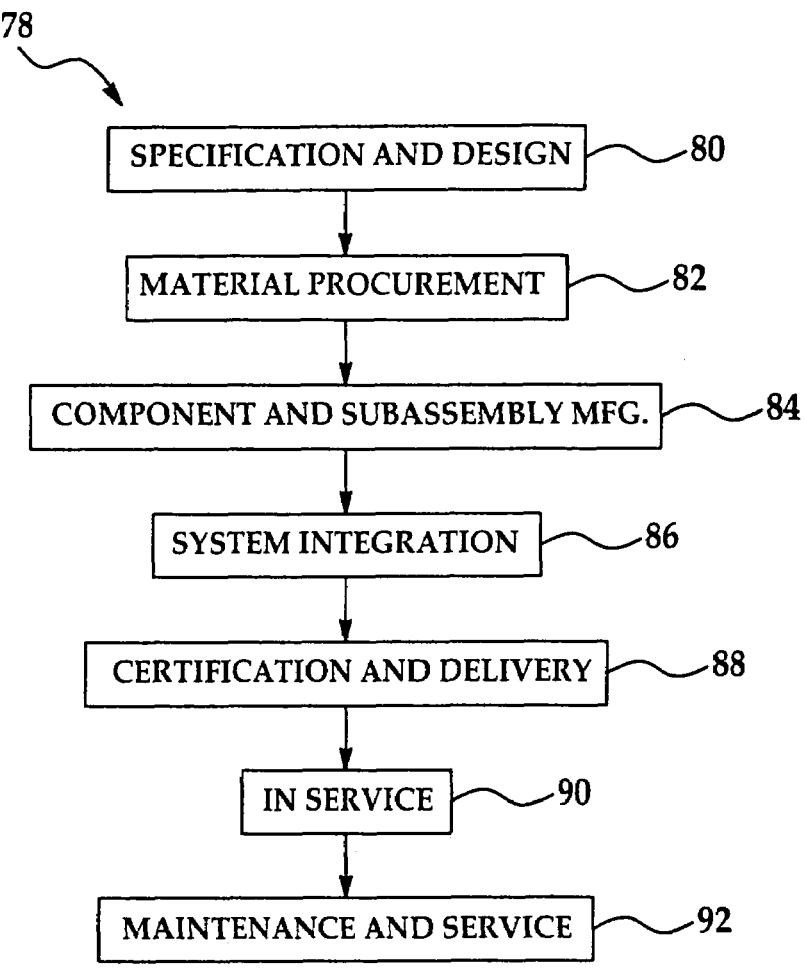
FIG. 10 is a flow diagram of an aircraft production and service methodology.
Figure 11:
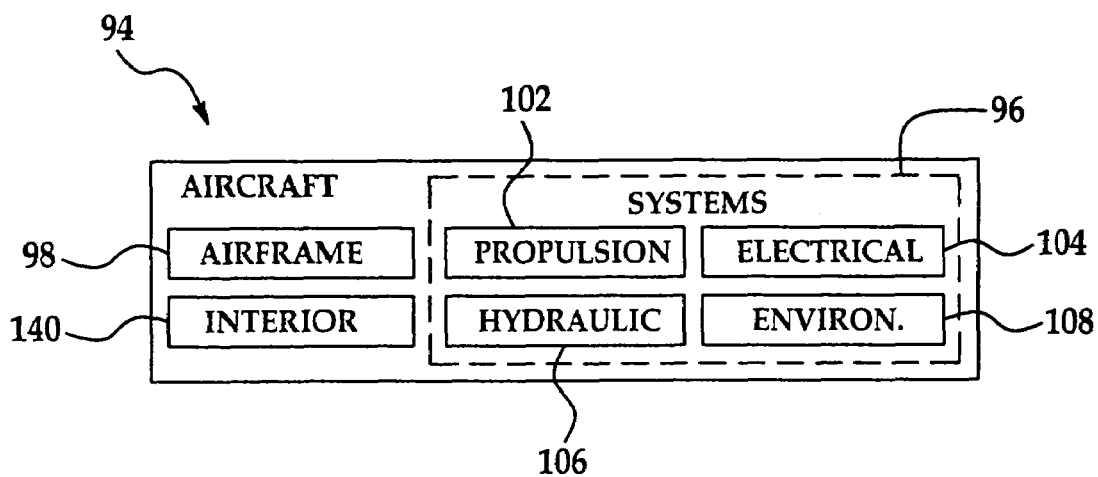
FIG. 11 is a block diagram of an aircraft.

Referring next to FIGS. 10 and 11, embodiments of the disclosure may be used in the context of an aircraft manufacturing and service method 78 as shown in FIG. 10 and an aircraft 94 as shown in FIG. 11. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 11, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A tensile specimen measuring apparatus, comprising:
   a generally elongated base;
   a generally elongated pin channel provided in said base;
   a measuring pin carrier slidably mounted in said pin channel of said base;
   at least one contact pin carried by said measuring pin carrier;
   at least one contact pin disposed at an end of said pin channel of said base in generally spaced-apart relationship with respect to said at least one contact pin carried by said measuring pin carrier; and
   an electronic measuring device engaging said at least one contact pin carried by said measuring pin carrier, said electronic measuring device for measuring a distance between said at least one contact pin carried by said measuring pin carrier and said at least one contact pin dispose at the end of said pin channel of the said base.

2. The apparatus of claim 1 further comprising a cover plate carried by said base and a generally elongated pin slot provided in said cover plate in generally registering relationship with respect to said pin channel and wherein said at least one contact pin carried by said measuring pin carrier and said at least one contact pin disposed at an end of said pin channel of said base extend through said pin slot.

3. The apparatus of claim 2 further comprising a plurality of base fastener openings provided in said cover plate, a plurality of plate fastener openings provided in said base and a plurality of plate fasteners extending through said plurality of base fastener openings and said plurality of plate fastener openings, respectively.

4. The apparatus of claim 1 wherein said measuring pin carrier comprises a pin carrier body slidably mounted in said pin channel of said base-and a pin opening provided in said pin carrier body, and wherein said at least one contact pin carried by said measuring pin carrier is seated in said pin opening.

5. The apparatus of claim 4 further comprising a generally elongated handle support extending from said pin carrier body and a handle provided on said handle support.

6. The apparatus of claim 1 wherein each of said at least one contact pin carried by said measuring pin carrier and said at least one contact pin disposed at an end of said pin channel comprises a generally elongated contact pin shaft and a pair of pin flanges provided on said contact pin shaft.

7. The apparatus of claim 6 wherein said pair of pin flanges comprises a pair of spaced-apart chamfered pin flanges.

8. The apparatus of claim 1 further comprising a measuring device cavity provided in said base and wherein said electronic measuring device is seated in said measuring device cavity.

9. A tensile specimen measuring apparatus, comprising:
   a generally elongated base;
   a measuring device cavity provided in said base;
   a generally elongated pin channel provided in said base and communicating with said measuring device cavity;
   a generally elongated cover plate carried by said base;
   a measuring device opening provided in said cover plate and generally registering with said measuring device cavity of said base;
   a pin slot provided in said cover plate and generally registering with said pin channel of said base;
   a measuring pin carrier slidably mounted in said pin channel of said base;
   at least one contact pin carried by said measuring pin carrier and extending through said pin slot;
   at least one contact pin disposed at an end of said pin channel of said base in generally spaced-apart relationship with respect to said at least one contact pin carried by said measuring pin carrier and extending through said pin slot; and
   an electronic measuring device seated in said measuring device cavity of said base and said measuring device opening of said cover plate and engaging said at least one contact pin carried by said measuring pin carrier.

10. The tensile specimen measuring apparatus of claim 9 wherein said measuring pin carrier comprises a pin carrier body slidably mounted in said pin channel of said base and a pin opening provided in said pin carrier body, and wherein said at least one contact pin carried by said measuring pin carrier is seated in said pin opening.

11. The apparatus of claim 10 further comprising a generally elongated handle support extending from said pin carrier body and a handle provided on said handle support.

12. The apparatus of claim 9 wherein each of said at least one contact pin carried by said measuring pin carrier and said at least one contact pin disposed at an end of said pin channel comprises a generally elongated contact pin shaft and a pair of pin flanges provided on said contact pin shaft.

13. The apparatus of claim 12 wherein said pair of pin flanges comprises a pair of spaced-apart chamfered pin flanges.

14. The apparatus of claim 9 further comprising a plurality of base fastener openings provided in said cover plate, a plurality of plate fastener openings provided in said base and a plurality of plate fasteners extending through said plurality of base fastener openings and said plurality of plate fastener openings, respectively.

15. A tensile specimen measuring method, comprising:
   providing an electronic measurement device;
   zeroing said electronic measurement device:
   providing a test specimen measuring apparatus having at least two contact pins;
   inserting a test specimen between said at least two contact pins of said test specimen measuring apparatus;
   measuring a parameter of said test specimen by drawing said test specimen between said at least two contact pins; and
   electronically recording a measurement reading displayed on said electronic measurement device.

16. The method of claim 15 wherein said test specimen measuring apparatus comprises a generally elongated base having a generally elongated pin channel and wherein said at least two contact pins are disposed at an end of said pin channel and said inserting a test specimen between said at least two contact pins comprises sliding at least one of said contact pins in said pin channel against said test specimen.

17. The method of claim 16 further comprising a measuring device cavity provided in said base and wherein said providing an electronic measurement device comprises seating said electronic measurement device in said measuring device cavity.

18. The method of claim 16 further comprising providing a cover plate having a measuring device opening on said base and wherein said seating said electronic measurement device in said measuring device cavity further comprises seating said electronic measuring device in said measuring device opening.

19. The method of claim 18 further comprising providing a pin slot in said cover plate and extending said contact pins through said pin slot.

20. The method of claim 19 further comprising providing a measuring pin carrier in said pin channel of said base and wherein at least one of said contact pins is carried by said measuring pin carrier.

* * * * *